(12) United States Patent
Reyneke et al.

(10) Patent No.: US 7,129,387 B2
(45) Date of Patent: Oct. 31, 2006

(54) LOW CAPITAL IMPLEMENTATION OF DISTRIBUTED DISTILLATION IN ETHYLENE RECOVERY

(75) Inventors: Rian Reyneke, Katy, TX (US); Michael J. Foral, Aurora, IL (US); Guang-Chung Lee, Houston, TX (US)

(73) Assignee: BP Corporation North America Inc., Warrenville, IL (US)

( * ) Notice: Subject to any disclaimer, the term of this patent is extended or adjusted under 35 U.S.C. 154(b) by 510 days.

(21) Appl. No.: 10/393,029

(22) Filed: Mar. 20, 2003

(65) Prior Publication Data
US 2004/0182751 A1    Sep. 23, 2004

(51) Int. Cl.
C07C 7/04 (2006.01)
B01D 3/14 (2006.01)

(52) U.S. Cl. .................. 585/809; 208/347; 203/99; 196/111; 202/158

(58) Field of Classification Search ............ 585/800; 203/99; 196/111; 202/158
See application file for complete search history.

(56) References Cited

U.S. PATENT DOCUMENTS

| | | | |
|---|---|---|---|
| 2,471,134 A | 5/1949 | Wright | |
| 5,675,054 A | 10/1997 | Manley et al. | |
| 5,709,780 A * | 1/1998 | Ognisty et al. | 202/158 |
| 5,755,933 A * | 5/1998 | Ognisty et al. | 202/158 |
| 6,077,985 A * | 6/2000 | Stork | 585/800 |
| 6,347,533 B1 * | 2/2002 | Tung | 62/620 |
| 6,514,387 B1 | 2/2003 | Emmrich et al. | |

FOREIGN PATENT DOCUMENTS

| | | |
|---|---|---|
| EP | 1 035 094 | 9/2000 |
| EP | 1 371 635 | 12/2003 |
| FR | 1546275 | 12/1967 |
| GB | 1194599 | 6/1970 |

OTHER PUBLICATIONS

Thermodynamically Optimal Method for Separating Multicomponent Mixtures, International Chemical Engineering (vol. 5, No. 3), Jul. 1965, pp. 555-561.
Optimize Ethylene Recovery, Hydrocarbon Processing, Apr. 1999, pp. 117-124.

* cited by examiner

Primary Examiner—Tam M. Nguyen
(74) Attorney, Agent, or Firm—James R. Henes

(57) ABSTRACT

An apparatus for recovering ethylene from a hydrocarbon feed stream, where the apparatus is a single distillation column pressure shell encasing an upper region and a lower region. The upper region houses an ethylene distributor rectifying section and the lower region houses a C2 distributor section and an ethylene distributor stripping section. Vapor passes from the lower region into the upper region, and liquid passes from the upper region to the lower region. The process for recovering the ethylene is also disclosed. The hydrocarbon feed stream is introduced into the C2 distributor section, and after a series of stripping and refluxing steps, distinct hydrocarbon products are recovered from the C2 distributor section, the ethylene distributor stripping section, and the ethylene distributor rectifying section, respectively.

5 Claims, 1 Drawing Sheet

LOW CAPITAL IMPLEMENTATION OF DISTRIBUTED DISTILLATION IN ETHYLENE RECOVERY

STATEMENT REGARDING FEDERALLY SPONSORED RESEARCH OR DEVELOPMENT

This invention was made with government support under United States Department of Energy Cooperative Agreement No. DE-FC07-01ID14090.

CROSS-REFERENCE TO RELATED APPLICATIONS

None.

BACKGROUND OF THE INVENTION

Distributed distillation has been suggested as a basis for the design of refinery systems, ethylene recovery systems, and other commercial chemical, petroleum and petrochemical separations systems operations for many years. Distributed distillation is best understood by contrasting it with sharp split distillation. In sharp split distillation, a separation is made between light and heavy components that are adjacent to each other on the volatility curve of the mixture being separated. That is, there are no compounds in the mixture that have volatility that is intermediate to those of the light and heavy components.

For example, a typical sharp-split deethanizer column in an ethylene recovery system performs a sharp split between ethane and propylene. The overheads of the column contain essentially no propylene and the bottoms contain essentially no ethane. The overheads therefore contain all components lighter than the light key component (e.g. ethylene, methane, etc.), and the bottoms contain all components heavier than the heavy component (e.g. propane, C4s, etc).

In a distributed distillation operation, a sharp split is not made between components that are adjacent on the volatility curve. A distributed distillation analog to the deethanizer is a "C2s distributor". A C2s distributor column produces a sharp split between methane and C3 components while distributing ethane and ethylene between the column overhead and bottoms. In a C2s distributor column, the light component is methane and the heavy component is propylene. These components are not adjacent to each other on the volatility curve; ethane and ethylene have a volatility that is intermediate between methane and propylene. In this case, then, ethane and ethylene "distribute" between the column overheads and bottoms. The overheads contain some ethane and ethylene, as well as methane and lighter components, but essentially no propylene. The bottoms also contain some ethane and ethylene, as well as propylene and heavier components, but essentially no methane. Of course, further purification of the components must be done in downstream columns.

A benefit of a distributed distillation system is that it requires less total energy to produce the final purified components than an analogous "sharp split" distillation sequence. A way of understanding the energy savings provided by distributed distillation is that it accomplishes the separation of components with fewer overall phase changes. Phase changes (condensation or vaporization) require energy, and reducing the number of phase changes also reduces the energy consumption of the system.

Thermal coupling of columns is another method for improving the overall energy efficiency of a distillation-based system. Thermal coupling of columns consists of providing liquid reflux to a column with a liquid side draw from a downstream column, or providing stripping vapor to a column with a vapor side draw from a downstream column. In this way, the composition of the reflux liquid at the top of the column is much closer to the equilibrium composition existing at the top of the column than could be produced by a typical condenser. Likewise, the composition of the stripping vapor sent to the bottom of the column is much closer to the equilibrium composition existing at the bottom of the column than if the vapor were generated with a conventional reboiler. This thermal coupling reduces the amounts of heavier components "remixed" into the bottom of the column and the amount of lighter components "remixed" into the top of the column. This improves the thermodynamic efficiency of the column, reducing reflux and reboil rates and thereby saving energy.

In addition, dividing wall columns have been recited in the prior art as a way to combine distinct distillation processes within a single pressure shell. Wright (U.S. Pat. No. 2,471,134) disclosed a partitioned fractionating column for separating components of a composite fluid in 1949. Petlyuk et al. (*Int. Chem. Eng.* 5, pp 555–561, 1965) disclosed a systematic discussion of dividing wall columns in 1965. The early dividing wall column designs included a dividing wall within the middle section of a column, with open, full-diameter rectifying and stripping sections in the top and bottom of the column, respectively. Oginsy (U.S. Pat. No. 5,709,780) disclosed a dividing wall column in which the vertical dividing wall extends from the middle section of the column all the way to the bottom of the column. The dividing wall therefore supplied the column with two stripping or absorption sections. Oginsy (U.S. Pat. No. 5,755,933) further disclosed a dividing wall column in which the vertical dividing wall extends from the middle section of the column all the way to the top of the column. The dividing wall in this case supplied the column with two separate rectifying sections.

Stork (U.S. Pat. No. 6,077,985) discloses the use of a dividing wall column for combining the deethanizing and deethyleneizing functions of an olefins plant separation train. This column design contains a dividing wall that extends from the middle section of a column all the way to the bottom of the column. The column is therefore split into two bottoms sections. Feed enters to the middle of one of these sections, which acts as a deethanizer column. The full-diameter rectifying section of the column acts as an ethylene rectifying section, and the section on the other side of the dividing wall acts as an ethylene stripper. However, both of the distillation functions disclosed by Stork utilize sharp-splits rather than distributed distillation.

Manley (U.S. Pat. No. 5,675,054) discloses the combined use of C2s distributors and ethylene distributors for the recovery of ethylene from cracked gas mixtures for a variety of feed types. Manley and Hahesy (*Hydrocarbon Processing*, April 1999, p 117) teaches combining separate rectifying sections into a single shell, and combining separate stripping sections into a single shell, but not combining rectifying and stripping sections from two separate distributed distillation columns into a single shell.

The present invention relates to a distillation column in which two distinct thermally coupled distributed distillation functions for ethylene recovery and purification are combined into a single shell. A separating wall within the single shell divides the column into zones in which the distinct distillation functions take place. This invention presents an apparatus that allows for a capital-efficient implementation of distributed distillation in the recovery and partial purification of ethylene. This invention further relates to the recovery of ethylene from a cracked gas stream through the use of distributed distillation, particularly through the combined use of a C2s distributor and an ethylene distributor.

Prior art designs utilize separate distillation columns for the C2s distributor and ethylene distributor functions. Two separate pressure vessels, foundations, and support structures are required to build and operate the prior art system. This invention is an improvement over the prior art in that both distillation functions are combined into a single pressure shell. Therefore, only one pressure vessel, foundation, and support structure is required using the design of this invention. This results in a significant reduction in both materials and installation costs compared with the prior art.

SUMMARY OF THE INVENTION

This invention recites an apparatus for the recovery and partial purification of ethylene from a hydrocarbon feed stream. A single distillation column pressure shell encases an upper region that has an ethylene distributor rectifying section and a lower region that has a C2 distributor section and an ethylene distributor stripping section. The apparatus has a means for collecting liquid flowing downward through the ethylene distributor rectifying section and for transporting the liquid to the C2 distributor section and the ethylene distributor stripping section. The C2 distributor section and the ethylene distributor stripping section are separated to prevent the passage of liquid or vapor between both sections. Vapor is passed from the lower region into the upper region, and the feed is introduced into the C2 distributor section.

This invention further recites a process for the recovery and partial purification of ethylene. At least one hydrocarbon feed stream is introduced into a distillation column pressure shell encasing an upper region housing an ethylene distributor rectifying section and a lower region housing a C2 distributor section and an ethylene distributor stripping section. The feed stream is introduced into the C2 distributor section. Stripping vapors are also introduced into the C2 distributor section and the ethylene distributor stripping section. Upflowing vapors from the C2 distributor and the ethylene distributor stripping section are introduced into the ethylene distributor rectifying section. The ethylene distributor rectifying section is refluxed, and distinct hydrocarbon products are recovered from the C2 distributor section, the ethylene distributor stripping section, and the ethylene distributor rectifying section.

The apparatus and process shall be described for the purposes of illustration only in connection with certain embodiments. However, it is recognized that various changes, additions, improvements and modifications to the illustrated embodiments may be made by those persons skilled in the art, all falling within the spirit and scope of the invention.

DETAILED DESCRIPTION OF THE INVENTION

Figure 1:
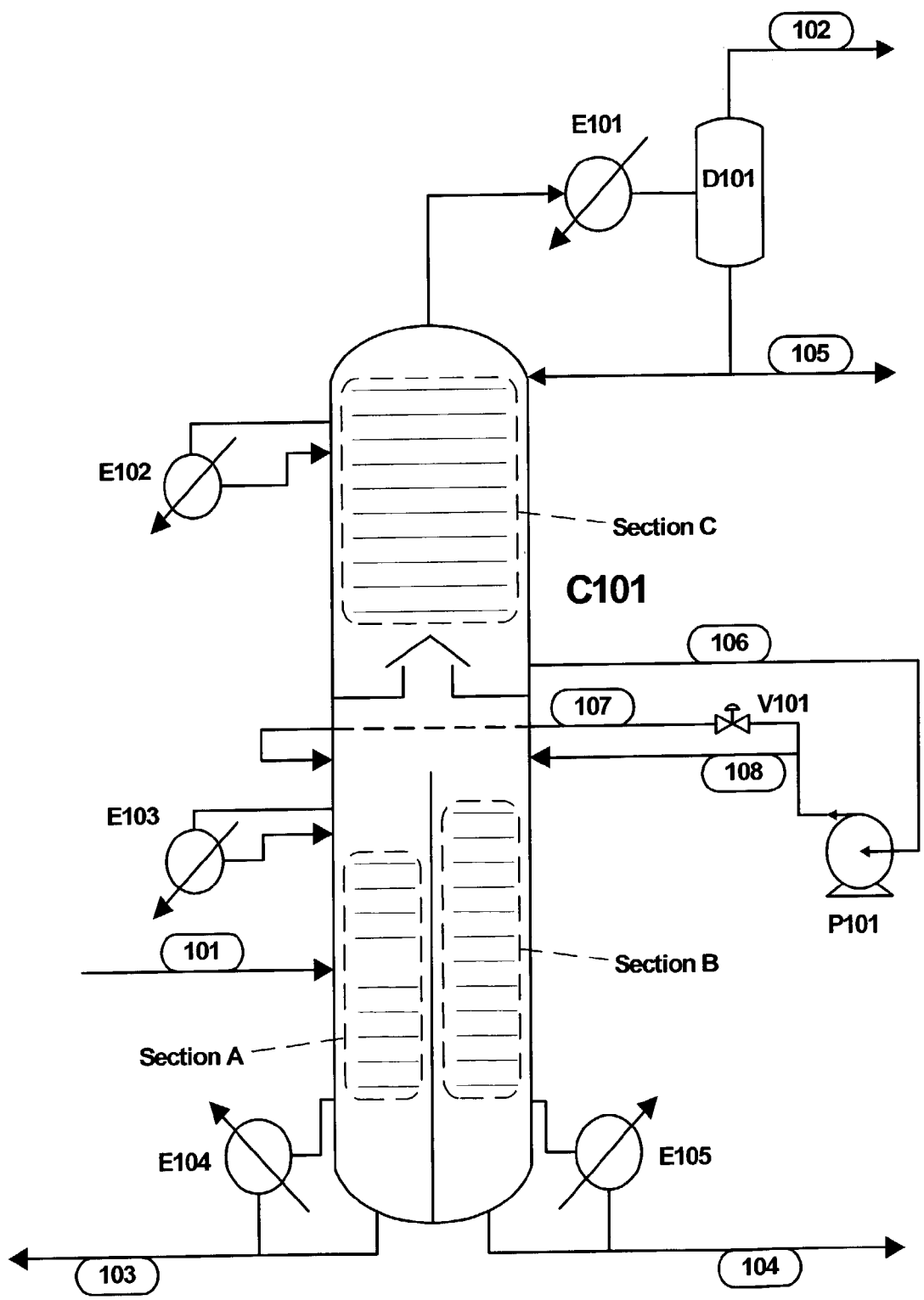
FIG. 1 depicts an embodiment of this invention in which two distillation functions are combined into a single shell which incorporates a dividing wall.

FIG. 1 depicts C2s distributor and ethylene distributor columns as combined into a single distillation column pressure shell. The single column is designated C101. A lower section of C101 is divided into two sub-sections by an impervious wall that prevents the transfer of liquids or vapors from one sub-section to the other. The sub-sections are designated as Section A and Section B in FIG. 1. The wall dividing the sections is typically thermally insulated to reduce the amount of heat transfer between the two sub-sections. Both Section A and Section B contain mechanical devices, such as contacting trays or packing, that enhance the contacting of liquids and vapors in each of the sections. Each section can contain a different type of mechanical vapor/liquid contacting device, or different numbers or designs of such devices, as is known to those skilled in the art.

The upper section of C101 above the dividing wall is designated as Section C in FIG. 1 and also contains mechanical devices such as contracting trays or packing that are designed to enhance the contact of liquid and vapor within this section. The overhead product of C101 is at least partially condensed in E101 and the liquid is separated from any uncondensed vapor in drum D101. At least a portion of the recovered liquid is used to provide reflux liquid that enters the top of Section C of column C101. Some of the condensed liquid may be removed via stream 105 as an overhead liquid product. Section C of C101 may also have one or more side condensers, shown as E102. Those skilled in the art will recognize that there are many potential designs for the overhead condensing system that are represented schematically by E101 and D101 and the side condensing system represented by E102 in FIG. 1. The specific design of these systems does not impact the nature of this invention.

Downflowing liquid that exits Section C is distributed between Sections A and B, and upflowing vapors exiting Sections A and B are combined and then enter Section C. Without limiting the nature of this invention, a typical arrangement for accomplishing the distribution of liquid and the combining of vapors is to situate a total liquid trap-out chimney tray situated below Section C and directly above the top of the dividing wall, as shown in FIG. 1. In such a design, all of the liquid exiting Section C is trapped on the chimney tray and thus prevented from directly entering Sections A and/or B. The liquid trapped on the chimney tray is removed via stream 106 and fed to pump P101, which provides the necessary pressure for flow control. The material from the pump outlet is divided into two streams, 107 and 108. Stream 107 is directed to the top of Section A, while stream 108 is directed to the top of Section B. The flow rate of streams 107 and 108 can be controlled through the use of flow control valve V101. Other means of splitting and controlling the flow of liquid to Section A and Section B can be used and are well known to those skilled in the art. If desired, additional condensers may be situated at or near the top of Section A to provide more liquid flow and/or a greater degree of control to this section. Such a condenser is shown as E103 in FIG. 1.

The vapors from Sections A and B are combined, for example, in an open space above the top of the dividing wall and below the total liquid trap-out chimney tray. They then pass through the chimney tray and enter a second open space above the chimney tray and below Section C. The vapors then continue to flow upwardly and enter the vapor/liquid contacting devices in Section C.

A feed stream, such as the overhead product of a depropanizer tower, enters column C101 via stream 101 to a point near the middle of Section A. It should be noted that multiple feed streams with multiple concentrations could enter Section A without altering the nature of this invention. In FIG. 1, a single feed to Section A divides Section A into a stripping section situated below the feed and above the section bottoms, and a rectifying section situated between the feed and the top of the dividing wall. The bottoms of Section A are reboiled using exchanger E104. The bottoms product from Section A exits via stream 103. The bottoms of Section B are reboiled using exchanger E105. The bottoms product from Section A exits via stream 104.

According to the present invention, Section A functions as a C2 distributor, Section B functions as the stripping section of an ethylene distributor, and Section C functions as the rectifying section of an ethylene distributor.

EXAMPLE 1

An apparatus of the invention resembling that shown in FIG. 1 was designed for a 1000KTA ethylene plant. The design of this example does not include exchangers E102 and E103, and no liquid overhead product (stream 105) is produced. The feed for this example is a vapor from the overhead of a depropanizer column (not shown in the Figure) and contains hydrogen, methane, ethylene, ethane, propylene and propane. In this example, Section C contains 70 theoretical stages, Section A contains 34 theoretical stages, and Section B contains 30 theoretical stages. The feed enters Section A at a point 20 theoretical stages above the bottom of Section A.

The diameter of the combined column in this example is 13.5 feet, the height is 222 feet, and it operates at a top pressure of 500 psig. The C2s distributor of Manley '054 is a dual-diameter column with an upper section diameter of 11 feet, a lower section diameter of 6.5 feet, an overall height of about 100 feet, and a top pressure of 500 psi. The ethylene distributor of Manley '054 is approximately 13 feet in diameter, 240 feet tall and operates at a top pressure of 500 psig. Comparing the installed equipment cost for the single column of this invention with the two columns of Manley '054 indicates that the single column of this invention can save approximately US $2.5 million over Manley '054.

Table 1 provides compositions and conditions for this example. The feed enters C101 via feed stream 101. Sufficient stripping vapor is generated by E104 to strip all of the methane and lighter components from the liquid bottoms product, stream 103. Stream 103 therefore contains essentially only propane, propylene, ethane, and ethylene.

Sufficient liquid is fed from Section C to the top stage of Section A to remove all propylene and heavier components from the vapor leaving Section A. The vapor leaving Section A therefore contains essentially only ethylene, ethane, and components lighter than ethylene. Sufficient liquid is fed to the top of Section C (generated by exchanger E101) to remove all of the ethane from the vapor leaving the top of Section C. The overhead product of the column, stream 102, therefore contains essentially only ethylene and components lighter than ethylene.

The liquid leaving Section C that is not fed to the top of Section A is fed to the top of Section B. Sufficient stripping vapor is generated in E105 to strip all of the methane and lighter components out of the liquid leaving the bottom of Section B. Therefore, the bottoms liquid of Section B, stream 104, contains essentially only ethane and ethylene.

TABLE 1

Flows and Conditions for Streams in FIG. 1

|  | Stream No. | | | | Vapor from Section |
| --- | --- | --- | --- | --- | --- |
|  | 101 | 102 | 103 | 104 | A |
| Temperature (Deg F.) | 5.0 | −80.7 | 70.2 | 33.7 | −24.1 |
| Pressure (psia) | 515 | 500 | 515 | 513 | 510 |
| Molar flows (lb mol/hr) | | | | | |
| HYDROGEN | 8597 | 8597 | 0 | 0 | 8737 |
| METHANE | 4714 | 4713 | 0 | 1 | 5221 |
| ETHYLENE | 9355 | 4417 | 1462 | 3476 | 12456 |
| ETHANE | 2506 | 1 | 682 | 1823 | 3964 |
| PROPYLENE | 884 | 0 | 882 | 2 | 4 |
| PROPANE | 206 | 0 | 206 | 0 | 0 |

We claim:

1. A process for the recovery and partial purification of ethylene from at least one feed stream introduced into a distillation column pressure shell encasing an upper region comprising an ethylene distributor rectifying section and a lower region comprising a C2 distributor section and an ethylene distributor stripping section, said feed stream comprising ethylene, ethane, a component or components lighter than ethylene, and optionally C3 and heavier components comprising:
   a. Introducing said feed stream into said C2 distributor section;
   b. Providing a means for introducing stripping vapor into said C2 distributor section;
   c. Introducing upflowing vapors from said C2 distributor section and said ethylene distributor stripping section into said ethylene distributor rectifying section;
   d. Providing a means for introducing stripping vapor into said ethylene distributor stripping section;
   e. Introducing downflowing liquid from said ethylene distributor rectifying section into said C2 distributor section and said ethylene distributor stripping section;
   f. Refluxing said ethylene distributor rectifying section;
   g. Recovering a stream of ethylene, ethane and C3+components from the bottom of said C2 distributor section;
   h. Recovering a stream of ethane and ethylene from the bottom of said ethylene distributor stripping section; and
   i. Recovering a stream of ethylene and components lighter than ethylene from the overhead of said ethylene distributor rectifying section.

2. The process of claim 1 wherein a wall separates said C2 distributor section and said ethylene distributor stripping section.

3. The process of claim 1 wherein said C2 distributor section, said ethylene distributor rectifying section, and said ethylene distributor stripping section each comprise a mechanical means for enhancing the contact of upflowing vapor and downflowing liquid.

4. The process of claim 1 wherein said distillation column pressure shell operates at a pressure from about 400 psia to about 550 psia.

5. The process of claim 1 wherein a liquid separation device situated above said lower region and beneath said upper region prevents liquid exiting said upper area from directly entering said C2 distributor and said ethylene distributor stripping sections.

* * * * *